United States Patent [19]

Fang

[11] Patent Number: 5,024,225
[45] Date of Patent: Jun. 18, 1991

[54] PERSONAL HEALTH MONITOR ENCLOSURE

[76] Inventor: William Fang, 1677 Apache Dr., Naperville, Ill. 60540

[21] Appl. No.: 461,249

[22] Filed: Jan. 5, 1990

[30] Foreign Application Priority Data

Sep. 26, 1989 [CA] Canada .................................. 613,116

[51] Int. Cl.$^5$ .............................................. A61B 5/04
[52] U.S. Cl. ............................... 128/630; 364/413.02; 364/413.06; 174/50; 128/696
[58] Field of Search ............... 128/630, 696, 668, 710, 128/732, 670; 364/413.02, 413.03, 413.04, 413.05, 413.06; 174/50

[56] References Cited

U.S. PATENT DOCUMENTS

| | | | |
|---|---|---|---|
| 4,571,456 | 2/1986 | Paulsen et al. | 179/2 |
| 4,583,553 | 4/1986 | Shah et al. | 128/704 |
| 4,679,144 | 7/1987 | Cox et al. | 128/710 |
| 4,715,385 | 12/1987 | Cudahy et al. | 128/710 |
| 4,730,364 | 3/1988 | Tat-Kee | 16/337 |
| 4,731,726 | 3/1988 | Allen, III | 364/416 |
| 4,736,332 | 4/1988 | Crease | 364/708 |
| 4,777,960 | 10/1988 | Berger et al. | 128/670 |
| 4,800,495 | 1/1989 | Smith | 364/413.03 |
| 4,803,625 | 2/1989 | Fu et al. | 364/413.03 |
| 4,928,704 | 5/1990 | Hardt | 128/732 |

Primary Examiner—Francis Jaworski
Assistant Examiner—George Manuel
Attorney, Agent, or Firm—Willian Brinks Olds Hofer Gilson & Lione

[57] ABSTRACT

In a personal health monitor of the type which includes a personal computer capable of implementing a program to determine one or more clinical parameters of the patient and further in which the personal computer includes a display screen portion that folds up from a keyboard portion, an improvement including a housing having a compartment of a size to contain the keyboard portion of the personal computer and to allow the display screen portion of the personal computer to extend above the housing, a keyboard cover capable of covering the keyboard portion of the personal computer in order to prevent access to the keyboard portion of the personal computer and maintain the display screen portion up from the keyboard portion and an input panel capable of conveying input to the personal computer.

19 Claims, 2 Drawing Sheets

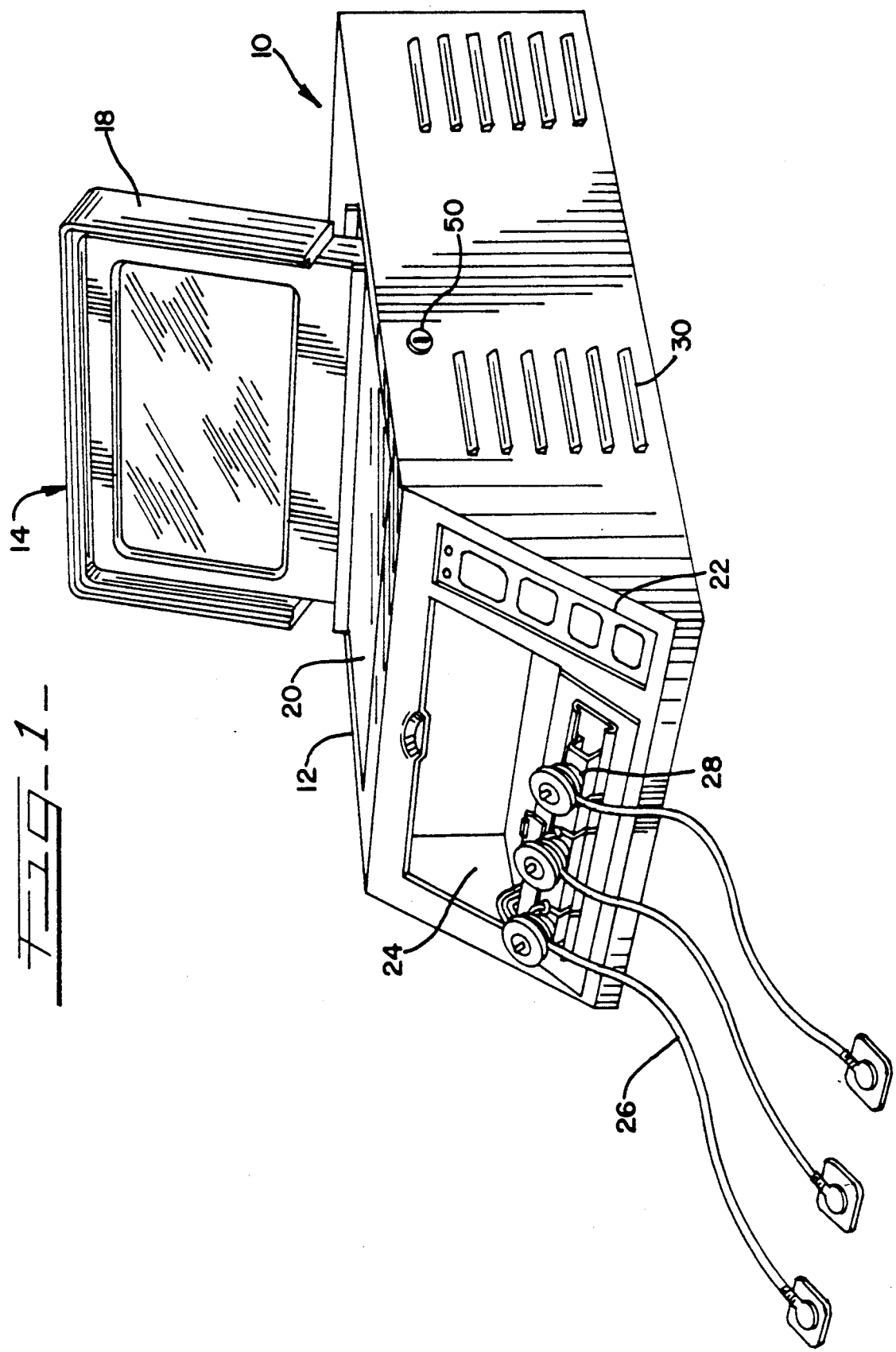

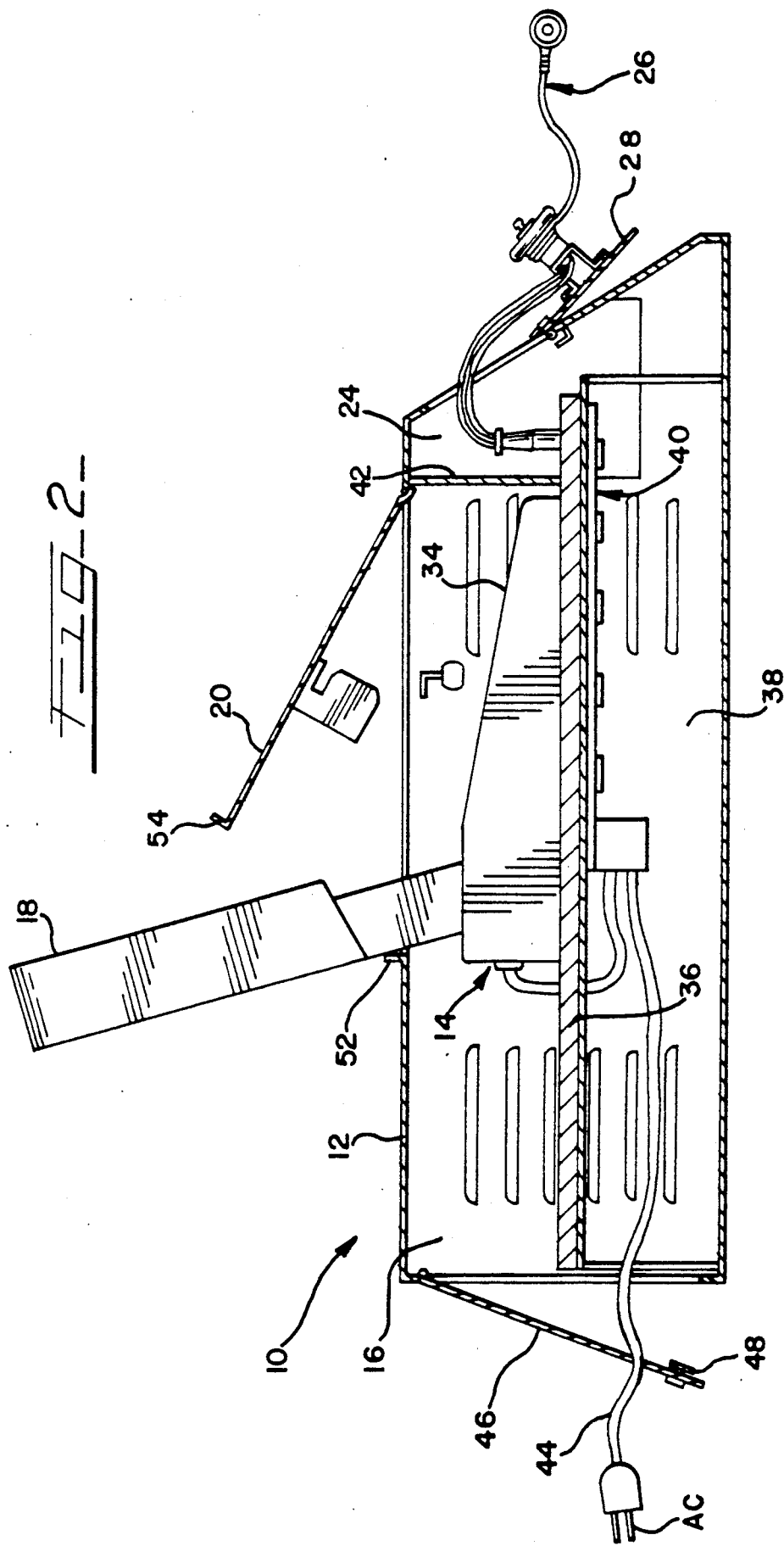

PERSONAL HEALTH MONITOR ENCLOSURE

BACKGROUND OF THE INVENTION

This invention relates to personal health monitors and more particularly to an improved enclosure for personal health monitors.

A personal health monitor is a device used to measure and record one or more clinical parameters of a patient for later transmission to the patient's physician or other health care provider. The personal health monitor may be used in a hospital or clinical setting as an adjunct to existing care. However, the personal health monitor may also be used by the patient himself in his own home. When used by a patient in his own home, the patient operates the personal health monitor to record certain of his own clinical parameters for subsequent transmission by the personal health monitor to the patient's physician or other health care provider. The personal health monitor, therefore, may be used by the patient who has a condition requiring monitoring of one or more clinical parameters but who otherwise does not require the level of care such as provided by a hospital. In such a circumstance, the personal health monitor provides potential savings in medical costs involved with a hospital stay. A personal health monitor of the type considered herein is described more fully in U.S. Pat. No. 4,803,625.

The personal health monitor may include one or more test components, or sensors, a programmable computer such a general purpose personal computer, and an interface connecting the sensors with the personal computer. In the above referenced patent, the programmable computer is a laptop personal computer having a display screen, keyboard, CPU (central processing unit), disk drive, and a means for connecting to the interface such as through a port, expansion slot, bus or other means.

A program on the computer affords an interactive, user-friendly way for the patient to interact with the personal health monitor to measure one or more clinical parameters. For purposes of this application, clinical parameters include physiological parameters, (such as vital signs like ECG, blood pressure, temperature, and weight), medication compliance and volunteered patient replies. The program can be specifically tailored to the patient's individual needs.

With the sensors a patient can measure one or more specific physiological parameters. The interface connects to the sensors and converts the signals from the sensors for storage as data by the personal computer. This data can later be transmitted for review by the patient's physician or other health care provider, as for example by modem or transportable storage medium.

In accordance with the testing regime established by the patient's physician, the personal health monitor may be used on a specific schedule to conduct sessions to measure certain of the patient's clinical parameters following instructions provided by the personal health monitor. In the embodiment described in the above referenced patent, the personal health monitor includes a personal computer with a display screen portion that can provide instructions for conducting a session in which clinical parameters are determined. For example, the program on the personal computer can provide instructions for measuring a patient's blood pressure or ECG. In addition, the personal health monitor can also present the patient with a series of questions about his health and prompt the patient for responses. For example, the patient can be asked to volunteer replies in response to a structured series of questions (e.g., "Do you have a fever?" followed by "If so, is your fever continuous or intermittent?"). The personal health monitor can be programmed to sound a reminder to initiate a testing session and record whether the patient adheres to the established schedule.

The personal health monitor can be used to give the patient instructions for taking medicines and provide the patient with reminders to take medications. Moreover, the personal health monitor can allow a physician to readily modify a medication schedule. For example, based upon the physiological parameters gathered by the personal health monitor and reviewed by a patient's physician, the physician may decide to alter the medication.

As described in the above referenced patent, the personal health monitor may include means for data storage so that the clinical parameters measured can be stored as data. The personal computer may include a modem so that the data can be transmitted to a central station. The data transmission can be done automatically by a program on the personal computer. The physician or other health care provider can then obtain the information from the central station either by calling, downloading or other means of communication. Alternately, a health care provider may be able to access the personal health monitor directly.

An advantage of the personal health monitor is that a high level of patient surveillance can be provided, even with the patient outside of a hospital or other expensive facility. Thus, the personal health monitor has the capability of lowering health care costs while at the same time maintaining or even improving the level of patient surveillance. Additional benefits include being able to return a patient to his home environment sooner and also providing a means for involving the patient in his own health program.

In order that the personal health monitor is efficient and adaptable in design, modular components are used whenever possible. For example, for the programmable computer component of the personal health monitor, a general purpose laptop personal computer can be utilized. Such computers are widely available, reliable and provide many of the functions needed by the personal health monitor. As mentioned above, the display screen portion of the personal computer can provide detailed and easy-to-understand-instructions. Moreover, initialization of the personal health monitor and setup of the program on the personal computer can readily be accomplished by trained personnel with access to the keyboard portion of the personnel computer. However, a drawback with using a general purpose personal computer is that its operation can be altered readily by anyone with access to the keyboard. Moreover, a personal computer keyboard may be intimidating or confusing to some patients and thereby discourage them from using the personal health monitor as needed.

Another drawback is that the sensors for measuring physiological parameters and the interface adapted to connect the sensors to the personal computer may include a variety of components and wires that may be confusing and further intimidating to a patient.

Accordingly it is an object of the present invention to provide a housing that contains the components of the personal health monitor system.

It is another object of the present invention to provide an enclosure for a personal health monitor that prevents unauthorized access to programmable components.

It is still another object of this invention to provide an easy to use way to provide input to the personal health monitor.

It is yet another object of the invention to provide a personal health monitor enclosure that includes compartments for one or more sensors, a personal computer, and the interface between the one or more sensors and the personal computer.

It is a still further object of the invention to provide a personal health monitor enclosure structure that is easy to assemble and maintain.

SUMMARY OF THE INVENTION

To achieve the foregoing and other objectives and in accordance with the purposes of the present invention, as embodied and broadly described herein, the present invention provides an improvement for a personal health monitor. In a personal health monitor of the type which includes a computer capable of implementing a program to determine one or more clinical parameters of a patient and further in which the computer includes a display screen portion that folds up from a keyboard portion, the improvement comprises a housing that includes a compartment of a size adapted to contain the keyboard portion of the personal computer and allow the display screen portion of the personal computer to extend above the housing, a keyboard cover capable of covering the keyboard portion of the personal computer in order to prevent access to the keyboard portion, and an input panel capable of conveying input to the personal computer.

BRIEF DESCRIPTION OF THE DRAWINGS

FIG. 1 is a perspective view of a personal health monitor that incorporates a preferred embodiment of this invention.

FIG. 2 is a vertical sectional view the embodiment of the invention depicted in FIG. 1.

DETAILED DESCRIPTION OF THE PREFERRED EMBODIMENT

Referring to FIG. 1, there is shown a personal health monitor 10 that can be used to monitor one or more clinical parameters of a patient for later review by the patient's physician or other health care provider. In the preferred embodiment, personal health monitor 10 includes a personal computer, sensors and an interface between the personal computer and the sensors. Personal health monitor 10 includes housing 12 that contains the personal computer, the sensors and the interface. Housing 12 is of sufficient dimensions so that a personal computer 14 can be accommodated within housing 12. Housing 12 may be made of metal, plastic or a similar material, or a combination of such materials. Personal computer 14 is of the lap-top type that folds open for use, with a display screen in the upper part and the keyboard section in the lower part. As shown in FIG. 1, personal computer 14 is positioned in housing 12 with the display screen portion 18 extending up and out of housing 12 so that a patient using the personal health monitor can readily follow prompts on display screen portion 18. Personal computer 14 may be of the type manufactured by Tandy, Toshiba or NEC. Computer 14 occupies a first compartment 16 in housing 12.

A first compartment cover 20 prevents access to the keyboard portion of personal computer 14 When closed. Thus, a patient normally does not use the keyboard provided with the personal computer 14. Instead, the patient's interaction with the computer is provided with the input panel 22, which may include touch buttons. Input panel 22 provides a simplified user-friendly interface for a person using the personal health monitor. First compartment cover 20 also maintains the display screen portion 18 of personal computer 14 in an upright portion or at least prevents it from closing on keyboard portion.

Personal health monitor 10 also includes a second compartment 24 for storage of sensors 26. Sensors 26 depicted in FIG. 1 are ECG leads and pads which a patient would affix to his body during a testing session in order to take an ECG test. Sensors 26 may also include a temperature probe and a blood pressure cuff which also may be stored in compartment 24 When not in use. The second compartment door 28 is shown in an open position in FIG. 1. Second compartment door 28 can be closed when the personal health monitor is not in use. Housing 12 also includes vents 30 in the side panels of housing 12 for the purpose of ventilating the equipment inside.

Referring to FIG. 2, there is depicted a sectional view of the personal health monitor. As shown in FIG. 2, the personal computer 14 occupies part of first compartment 16. The keyboard portion 34 of computer 14 is beneath first compartment door 20 (shown here in a partially opened position). First compartment 16 is defined by a partition in housing 12 which here is shown as slidable drawer 36. Slidable drawer 36 is inserted through channels in the sides of housing 12 from the rear of housing 12. Slidable drawer 36 also defines a third compartment 38 herein used to contain the interface 40. Another panel 42 affixed to the upper side of drawer 36 provides a partition defining the sensor compartment 24 and partitions it from first compartment 16. Openings (not shown) are cut out in drawer 36 and allow connection of sensors 26 to interface 40 and also allow connection of interface 40 to personal computer 14. A line 44 for AC power is connected to the interface 40. Line 44 extends out the back of housing 12. A rear panel door 46 hinged at the top allows access to the interior of housing 12 for servicing and permits removal of drawer 36. Rear panel door 46 has an opening in it through which the line 44 for AC may extend. A lock 48 is provided in rear panel door 46 for locking the rear panel door 46 to prevent unauthorized access to the interior of housing 12. A similar lock 50 shown in FIG. 1 can prevent unauthorized opening of first compartment cover 20 thereby preventing unauthorized access to the keyboard of computer 14.

With the personal health monitor housing as described herein, assembly of the personal health monitor is made efficient. The interface 40 can be completely assembled and tested while attached to the drawer 36 prior to installation into the personal health monitor housing 12. If maintenance is required, the interface 40 can be easily removed by removing the drawer 36.

Prior to use by the patient, the program on the personal computer 14 is tailored for the individual patient's needs. The first compartment cover 20 is locked by lock 50 and the rear panel door 46 is locked by lock 48 to prevent unauthorized access to either the keyboard portion 34 of the personal computer 14 or the interface 40. During use by the patient, the patient will use the input panel 22 to provide input to the personal health monitor.

It is therefore intended that the foregoing detailed description be regarded as illustrative rather than limiting, and that it be understood that it is the following claims, including all equivalents, which are intended to define the scope of the invention.

I claim:

1. In a personal health monitor of the type comprising a personal computer capable of implementing a program to determine one or more clinical parameters of a patient and further in which the personal computer includes a display screen portion that folds up from a keyboard portion, an improvement comprising:
    a housing that comprises:
        a first compartment of a size adapted to contain the keyboard portion of the personal computer and allow the display screen portion of the personal computer to extend above said first compartment,
        a keyboard cover capable of covering the keyboard portion of the personal computer while the display screen portion of the personal computer is extended into position above said first compartment in order to prevent access to the keyboard portion while the display screen portion is viewable by the patient, and
        an input panel located outside of said first compartment and capable of conveying input signals from the patient to the personal computer.

2. The improvement for a personal health monitor as set forth in claim 1 in which the personal health monitor also includes one or more sensors capable of determining one or more physiological parameters of a patient and an interface between the one or more sensors and the personal computer to enable the personal computer to record the parameters determined by the sensors, and in which said housing further comprises:
    a second compartment for containing the one or more sensors.

3. The personal health monitor improvement of claim 2 in which said housing further comprises:
    a third compartment for containing the interface.

4. The personal health monitor improvement of claim 3 in which said housing further comprises:
    a drawer panel for partitioning said housing in the interior thereof and defining a bottom of said first compartment, said drawer panel fixed in said housing in channels and further in which said drawer panel is slidably removable from said housing.

5. The personal health monitor improvement of claim 4 in which said drawer panel is capable of removal by sliding out a rear side of said housing.

6. The personal health monitor improvement of claim 5 in which said drawer panel also comprises an interior panel portion mounted on an upper side of said drawer panel, said interior panel portion adapted to define a rear wall of said second compartment.

7. The personal health monitor improvement of claim 6 in which said drawer panel also defines said third compartment beneath said drawer panel between the lower side of said drawer panel and the interior bottom of said housing and further in which said drawer panel is constructed and adapted so that the interface is capable of being mounted on said drawer panel whereby the interface can be removed for servicing by removal of said drawer panel out the rear of said housing.

8. The personal health monitor improvement of claim 7 in which said housing further comprises:
    a rear door to prevent access to said first compartment and said third compartment when said rear door is in a closed position and to allow access to said first compartment and said third compartment and further to allow removal of said slidable drawer when said rear door is in an open position.

9. The personal health monitor improvement of claim 8 in which said housing further comprises:
    a rear door lock capable of locking said rear door.

10. The personal health monitor improvement of claim 2 in which said housing further comprises:
    a sensor compartment door located on a front of said housing and permitting access to said second compartment.

11. The personal health monitor improvement of claim 10 in which said housing further comprises
    a front panel in which is located said sensor compartment door and on which is located said input response panel.

12. The personal health monitor improvement of claim 11 in which the lower edge of said sensor compartment door is hingedly attached to said front panel whereby said sensor compartment door will remain in an open position allowing access to said second compartment when opened for use of the one or more sensors.

13. The personal health monitor improvement of claim 12 in which the one or more sensors are mounted on said sensor compartment door on an inner side thereof whereby the one or more sensors can be utilized when said sensor compartment door is in an open position.

14. The personal health monitor improvement of claim 2 in which said housing further comprises one or more sides having ventilation slots therein.

15. The personal health monitor improvement of claim 1 in which said keyboard cover defines an opening to allow the display screen portion of the personal computer to extend above said housing and further in which the personal health monitor improvement comprises:
    flanges located around the opening defined by said keyboard cover, said flanges extending upward from the opening whereby the display monitor portion of the personal computer can be propped up to extend out of said first compartment and further whereby spillage of liquids into the interior of the personal health monitor can be prevented.

16. The personal health monitor improvement of claim 1 in which said housing further comprises:
    a keyboard cover lock whereby opening of said keyboard cover can be prevented.

17. A housing for a personal health monitor comprising:
    a first compartment of a size adapted to contain the keyboard portion of a laptop personal computer and allow the display screen portion of the laptop personal computer to extend above said first compartment,
    a keyboard cover capable of covering the keyboard portion of the laptop personal computer while the display screen portion of the personal computer is extended into position above said first compartment in order to prevent access to the keyboard portion while the display screen portion is viewable, and an input panel capable of conveying input signals to the laptop personal computer.

18. The housing of 17 further comprising:
a second compartment for containing one or more sensors capable of determining one or more physiological parameters of a patient.

19. The housing of claim 18 further comprising:
a third compartment for containing an interface between the one or more sensors and the personal computer to enable the personal computer to record the parameters determined by the sensors.

* * * * *

UNITED STATES PATENT AND TRADEMARK OFFICE
CERTIFICATE OF CORRECTION

PATENT NO. : 5,024,225
DATED : June 18, 1991
INVENTOR(S) : William Fang

It is certified that error appears in the above-indentified patent and that said Letters Patent is hereby corrected as shown below:

Column 2, line 54 delete "personnel" and substitute therefor --personal--.

In the Drawings:
Column 3, line 41, after "view" insert --of--.

Column 4, line 2, delete "When" and substitute therefor -- when--.
Column 4, line 19, delete "When" and substitute therefor --when--.
Column 4, lines 46 and 47, delete "remoVal" and substitute therefor --removal--.
Column 6, line 2, claim 11, after "comprises" insert --:--.

Signed and Sealed this

Twenty-eighth Day of September, 1993

Attest:

BRUCE LEHMAN

*Attesting Officer*    *Commissioner of Patents and Trademarks*